US006436950B1

(12) United States Patent
Achari et al.

(10) Patent No.: US 6,436,950 B1
(45) Date of Patent: Aug. 20, 2002

(54) NASAL DELIVERY OF APOMORPHINE

(75) Inventors: Raja G. Achari, Millington, NJ (US); Shamim Ahmed, Central Islip, NY (US); Charanjit R. Behl, Hauppauge, NY (US); Jorge C. deMeireles, Syosset, NY (US); Tianquing Liu, Central Islip, NY (US); Vincent D. Romeo, Massapequa Park, NY (US); Anthony P. Sileno, Brookhaven Hamlet, NY (US)

(73) Assignee: Nastech Pharmaceutical Company, Inc., Hauppauge, NY (US)

( * ) Notice: Subject to any disclaimer, the term of this patent is extended or adjusted under 35 U.S.C. 154(b) by 0 days.

(21) Appl. No.: 09/334,304

(22) Filed: Jun. 16, 1999

Related U.S. Application Data

(60) Provisional application No. 60/096,545, filed on Aug. 14, 1998.

(51) Int. Cl.[7] ............................................. A61K 31/44
(52) U.S. Cl. ....................................................... 514/284
(58) Field of Search ........................................ 514/284

(56) References Cited

U.S. PATENT DOCUMENTS

| 5,756,483 A | 5/1998 | Merkus | 514/58 |
| 5,770,606 A | 6/1998 | El-Rashidy et al. | 514/284 |
| 5,773,020 A | 6/1998 | Place et al. | 424/426 |

FOREIGN PATENT DOCUMENTS

| GB | WO 99/27905 | 6/1999 |
| WO | wo 99/66933 | 12/1999 |

OTHER PUBLICATIONS

Muñoz et al., "Long–term treatment with intermittent intranasal or subcutaneous apormorphine in patients with levodopa–related motor fluctuations", Clin Neuropharmacol 1997 Jun:20(3):245–52.

Van Laar T et al., "Nasolabial allergic reaction to intranasal administration of apomorphine in Parkinson disease", Ned Tijdschr Geneeskd. Apr. 4, 1992;136(14):702–4. Dutch.(Abstract in English).

Heaton et al., "Recovery of erectile function by the oral administration of apomorphine", Urology. Feb. 1995;45(2):200–6.

*Primary Examiner*—Theodore J. Criares
*Assistant Examiner*—Jennifer Kim
(74) *Attorney, Agent, or Firm*—Woodcock Washburn LLP

(57) ABSTRACT

Intranasal delivery methods and compositions for the delivery of dopamine receptor agonists are provided which are effective for the amelioration of erectile dysfunction in a mammal without causing substantial intolerable adverse side effects to the mammal. Nasally administered compositions for treating male erectile dysfunction in a mammal are also provided which include a therapeutically effective amount of a dopamine receptor agonist which has been dispersed in a system to improve its solubility and/or stability.

15 Claims, No Drawings

NASAL DELIVERY OF APOMORPHINE

This Application claims the benefit of U.S. Provisional Application No. 60/096,545 filed Aug. 14, 1998, the entirety of which is incorporated herein by reference.

BACKGROUND OF THE INVENTION

The present invention relates generally to intranasal delivery methods and dosage forms. More particularly, methods and dosage forms for the safe and reliable intranasal delivery of apomorphine to ameliorate erectile dysfunction in a mammal are provided.

Apomorphine is a potent dopamine receptor agonist which has a variety of uses. For example, it has been effectively used as an adjunctive medication in the treatment of Parkinson's disease which is complicated by motor fluctuations (T. van Laar et al., *Arch. Neurol.*, 49: 482–484 (1992)). In particular, apomorphine has been used for relieving "off-period" symptoms in Parkinson patients with such response fluctuations. In the study by van Laar et al., the intranasally applied apomorphine used to achieve the results reportedly included an aqueous solution of apomorphine hydrochloride (HCL) at a concentration of 10 mg/ml. This formulation is also used for parenteral application and is published in different Pharmacopeia's.

Also, U.S. Pat. No. 5,756,483 issued to Merkus (hereinafter "the '483 patent") which is hereby incorporated by reference, discloses the intranasal delivery of a variety of compositions, including apomorphine in combination with a cyclodextrin and/or a polysaccharide and/or a sugar alcohol for treating Parkinson's disease. The '483 patent, however, discloses very narrow dosage ranges of 0.1 to 2 mg of apomorphine per nostril which is specifically tailored for the amelioration of the "off-period" symptoms of Parkinson's disease.

Further, U.S. Pat. No. 5,770,606 issued to El-Rashidy et al. (hereinafter "the '606 patent"), which is hereby incorporated by reference, discloses the delivery of apomorphine in a sublingual dosage unit for alleviating psychogenic impotence or erectile dysfunction with no substantial undesirable side effects. The '606 patent further includes results from a study conducted by the inventors on the effect of apomorphine delivered intranasally on erectile dysfunction. The study suggested that intranasal delivery of apomorphine at concentrations of 2.5 mg to 3.5 mg was effective for eliciting an erection in patients suffering from erectile dysfunction, however, since the study participants suffered extensive and serious side effects including hypotension, nausea, vomiting, impaired vision, diaphoresis and ashen coloring, it was concluded that intranasal delivery of apomorphine to treat erectile dysfunction was insufficiently safe and reliable to be a viable commercial product.

Accordingly, it is one of the purposes of this invention, among others, to provide a safe and reliable intranasal delivery system for apomorphine that ensures delivery of therapeutic amounts of the drug into the bloodstream which is fast acting, easily administered and causes no substantial adverse side effects.

SUMMARY OF THE INVENTION

It has now been discovered that this and other purposes can be achieved by the present invention, which provides for a method for ameliorating male erectile dysfunction in a mammal. This method includes the nasal administration of a dopamine receptor agonist to the mammal before, during or after sexual activity in an amount sufficient to induce an erection without inducing substantial intolerable side effects in the mammal. Preferably, the dopamine receptor agonist is apomorphine.

The present invention also provides for a pharmaceutical composition for treating male erectile dysfunction in a mammal without causing substantial intolerable adverse side effects that includes a therapeutically effective amount of a dopamine receptor agonist in combination with a nasal delivery system. Preferably, the dopamine receptor agonist is selected from the group consisting of apomorphine, chemically modified equivalents and pharmaceutical salts thereof and even further preferably, the dopamine receptor agonist is apomorphine. The chemically modified equivalents of apomorphine preferably include a pro-drug. Further, it is preferable that apomorphine is dispersed in an aqueous or non-aqueous formulation.

In addition, the nasal delivery system of the pharmaceutical composition can include a buffer to maintain the pH of the dopamine receptor agonist, a pharmaceutically acceptable thickening agent and a humectant. The pharmaceutical composition can further include one or more pharmaceutical excipients and even further include a pharmaceutically acceptable preservative.

The buffer of the nasal delivery system can be selected from the group including acetate, citrate, prolamine, carbonate and phosphate buffers.

The thickening agent of the nasal delivery system can be selected from the group including methyl cellulose, xanthan gum, carboxymethyl cellulose, hydroxypropyl cellulose, carbomer, polyvinyl alcohol, alginates, acacia, chitosans and combinations thereof.

The humectant of the nasal delivery system can be selected from the group including sorbitol, glycerol, mineral oil, vegetable oil and combinations thereof.

The present invention also provides a method of treating erectile dysfunction in a male mammal including nasally administering a pharmaceutical composition including a therapeutically effective amount of a dopamine receptor agonist in combination with a nasal delivery system wherein the pharmaceutical composition does not cause substantial intolerable adverse side effects in the mammal.

The present invention also provides for a nasally administered pharmaceutical composition that includes a therapeutically effective amount of a dopamine receptor agonist dispersed in a buffer to maintain its pH, a pharmaceutically acceptable thickening agent and a humectant, wherein said nasally administered pharmaceutical composition does not cause substantial intolerable adverse side effects when administered to a mammal. The dopaamine receptor agonist of the nasally administered pharmaceutical composition is selected from the group including apomorphine, chemically modified equivalents and pharmaceutical salts thereof. It is further preferable that chemically modified equivalents of apomorphine include a pro-drug.

The present invention also provides for a method of treating impotence and male erectile dysfunction in a human in need of such treatment including administering to a nasal membrane of the human an effective amount of a nasally administered pharmaceutical composition including a therapeutically effective amount of a dopamine receptor agonist dispersed in a buffer to maintain its pH, a pharmaceutically acceptable thickening agent and a humectant, wherein the nasally administered pharmaceutical composition does not cause substantial intolerable adverse side effects when administered to the human.

Another preferred method of the present invention also provides for treating male erectile dysfunction in a mammal without causing substantial intolerable adverse side effects. This method includes administering into a nasal cavity of the mammal a therapeutically effective dosage of a dopamine receptor agonist in combination with a nasal delivery system. The nasal delivery system includes a pharmaceutically acceptable buffer, a thickening agent and a humectant. The dopamine receptor agonist is selected from the group including apomorphine, chemically modified equivalents and pharmaceutical salts thereof. Preferably, chemically modified equivalents of apomorphine include a pro-drug.

Another preferred method of the present invention is a method for administering a therapeutically effective amount of a dopamine receptor agonist to a mammal through a nasal membrane without causing substantial intolerable adverse side effects. This method includes delivering to the nasal membrane of a mammal a dopamine receptor agonist dispersed in a nasal delivery system which includes a pharmaceutically acceptable buffer, a thickening agent and a humectant. Preferably, the dopamine receptor agonist is effective for the treatment of male erectile dysfunction in a mammal.

The present invention also provides for an intranasal dosage unit for treating impotency or erectile dysfunction in a mammal which does not cause substantial intolerable adverse side effects. The dosage unit includes an effective amount of a dopamine receptor agonist in combination with an intranasal carrier. The intranasal carrier includes a buffer. The buffer pH is selected to enhance absorption of the dopamine receptor agonist and to produce an erection within about 60 minutes of administering the dosage unit to a nasal mucosa of the mammal. Preferably, an erection is produced within about 45 minutes, more preferably within about 30 minutes, most preferably within about 15 minutes, and even further preferably in less than about 15 minutes.

The intranasal carrier of the intranasal dosage unit is preferably an aqueous solution. Further, the aqueous solution can be selected from the group including aqueous gels, aqueous suspensions, aqueous liposomal dispersions, aqueous emulsions, aqueous microemulsions and combinations thereof.

Alternatively, the intranasal carrier of the intranasal dosage unit is a non-aqueous solution. The non-aqueous solution can be selected from a group including non-aqueous gels, non-aqueous suspensions, non-aqueous liposomal dispersions, non-aqueous emulsions and non-aqueous microemulsions and combinations thereof.

The intranasal carrier of the intranasal dosage unit can also be a combination of an aqueous solution and a non-aqueous solution.

Alternatively, the carrier of the intranasal dosage unit is a powder formulation. The powder formulation can be selected from a group including simple powder mixtures, powder microspheres, coated powder microspheres, liposomal dispersions and combinations thereof. Preferably, the powder formulation is powder microspheres. The powder microspheres are preferably formed from various polysaccharides and celluloses selected from the group including starch, methylcellulose, xanthan gum, carboxymethylcellulose, hydroxypropyl cellulose, carbomer, alginate polyvinyl alcohol, acacia, chitosans and combinations thereof The intranasal dosage unit can also include an excipient having bio-adhesive properties. Preferably, the buffer of the intranasal dosage unit is selected to have a pH of from about 3 to about 10 and more preferably from about 3.5 to 7.0.

Preferably, the intranasal dosage unit includes a humectant. A humectant can be selected from the group consisting of soothing agents, membrane conditioners, sweeteners and combinations thereof.

The present invention also provides for a nasally administered pharmaceutical composition for treating male erectile dysfunction in a mammal including a therapeutically effective amount of a dopamine receptor agonist which has been dispersed in a system to improve its solubility. The dopamine receptor agonist of this composition is selected from the group consisting of apomorphine, chemically modified equivalents and pharmaceutical salts thereof. The system of this composition includes one of the following or combinations thereof: a glycol derivative; a sugar alcohol; glycerin; propylene glycol and glycerin; polyethylene glycol 400; ascorbic acid and water; sodium ascorbate and water; or sodium metabisulfite and water. Preferred glycol derivatives include propylene glycol and polyethylene glycol. Preferred sugar alcohols include mannitol and xylitol.

The present invention also provides for a nasally administered pharmaceutical composition for treating male erectile dysfunction in a mammal including a therapeutically effective amount of a dopamine receptor agonist which has been dispersed in a system to improve its stability. The dopamine receptor agonist of this composition is selected from the group consisting of apomorphine, chemically modified equivalents and pharmaceutical salts thereof. The system of this composition includes one of the following or combinations thereof: a glycol derivative; a sugar alcohol; glycerin; propylene glycol and glycerin; polyethylene glycol 400; ascorbic acid and water; sodium ascorbate and water; or sodium metabisulfite and water. Preferred glycol derivatives include propylene glycol and polyethylene glycol. Preferred sugar alcohols include mannitol and xylitol.

These and other advantages of the present invention will be appreciated from the detailed description and examples which are set forth herein. The detailed description and examples enhance the understanding of the invention, but are not intended to limit the scope of the invention.

DETAILED DESCRIPTION OF THE INVENTION

The present invention is directed to compositions and methods for treating sexual dysfunction in a mammal. In particular, a method is provided for ameliorating male erectile dysfunction in a mammal by nasally administering to the mammal a therapeutically effective amount of a dopamine receptor agonist before, during or after sexual activity which is sufficient to induce an erection without causing substantial adverse side effects in the mammal.

For purposes of the present invention, the phrase "erectile dysfunction" is intended to encompass certain medically related symptoms resulting in the inability of a male to perform sexually, including penile dysfunction, as well as male impotence. As used herein, the term "impotence" is intended to mean the inability of a male to achieve and/or sustain a penile erection sufficient for vaginal penetration and intercourse.

As used herein, a "dopamine receptor agonist" is intended to encompass those members of the dopamine receptor agonist family which are able to ameliorate male erectile dysfunction when administered to a mammal. Apomorphine is an example of such a composition. Thus, the present invention is intended to encompass apomorphine and its functional equivalents including pharmaceutical salts and chemically modified equivalents thereof, including for example pro-drug forms of apomorphine. Apomorphine can be represented by the formula:

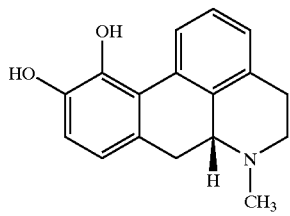

and in the present invention can exist in a free base form or as an acid addition salt. For the purposes of the present invention, apomorphine hydrochloride is preferred; however, other pharmacologically acceptable moieties thereof can be utilized as well. The term "apomorphine" as used herein includes the free base form of this compound as well as pharmacologically acceptable acid addition salts thereof. In addition to the hydrochloride salt of apomorphine, other pharmacologically acceptable acid addition salts of apomorphine include the hydrobromide, the hydroiodide, the bisulfate, the phosphate, the acid phosphate, etc.

For the purposes of the present invention, apomorphine or a similarly acting dopamine receptor agonist is administered nasally in an amount sufficient to excite cells in the mid-brain region of the patient but without substantial adverse side effects.

This cell excitation is believed to be part of a cascade of stimulation that is likely to include neurotransmission with serotonin and oxytocin. Because dopamine receptors agonists act directly on regions of the mid-brain, the present invention also contemplates the use of such agonists for improving the sexual desire in both male and female mammals, as well as the amelioration of erectile dysfunction in males as set forth above.

The dopamine receptors in the mid-brain region of a patient can be stimulated to a degree sufficient to cause an erection by the nasal administration of apomorphine so as to maintain an adequate plasma concentration of apomorphine. The amount of apomorphine nasally administered is an amount sufficient to cause an erection but is low enough not to cause substantial intolerable adverse side effects. As used herein, "substantial intolerable adverse side effects" include those effects caused by either the delivery system or the dopamine receptor agonist which are incompatible with the health of the user or which are so unpleasant as to discourage the continued use of the composition. Such effects include, for example, hypotension, nausea, vomiting, impaired vision, diaphoresis and ashen coloring.

Apomorphine is nasally administered about 30 to about 45 minutes prior to sexual activity, preferably about 15 to about 20 minutes prior to sexual activity, and more preferably less than 15 minutes prior to sexual activity.

The compositions according to the present invention can be administered, for example, as a nasal spray, nasal drop, suspension, gel, ointment, cream or powder. The administration of a composition can also include using a nasal tampon or a nasal sponge containing a composition of the present invention.

The dopamine receptor agonist can also be brought into a viscous basis via systems conventionally used, for example, natural gums, methylcellulose and derivatives, acrylic polymers (carbopol) and vinyl polymers (polyvinylpyrrolidone). In the present compositions, many other excipients known in the art can be added such as preservatives, surfactants, co-solvents, adhesives, antioxidants, buffers, viscosity enhancing agents and agents to adjust the pH and the osmolarity.

The amount of dopamine receptor agonist administered to a patient will vary according to the delivery system used, and the age and weight of the patient. There are two critical parameters for selecting the appropriate dosage levels of the dopamine receptor agonist. First, the dosage level must be effective for achieving an erection in the patient and second, the dosage level must not cause substantial intolerable adverse side effects to the patient.

The onset of substantial intolerable adverse side effects, for example, nausea and/or vomiting, can be obviated or delayed by nasally delivering a dopamine receptor agonist at a controlled dissolution rate so as to provide circulating serum levels and mid-brain tissue levels of the dopamine receptor agonist sufficient for an erection and without inducing nausea and/or vomiting. When it is necessary to administer higher doses of a dopamine receptor agonist, for example, doses above about 2 mg, the likelihood of a substantial intolerable adverse side effect onset can be reduced by concurrently administering a ganglionic agent capable of inhibiting the ganglionic response, for example, nicotine or lobeline sulfate.

Other antiemetic agents that can be used in accordance with the present invention include metoclopramide; phenothiazines such as chlorpromazine, prochlorperazine, pipamazine, thiethylperazine and oxypendyl hydrochloride; serotonin (5-hydroxytryptamine or 5-IIT) agonists such as domperidone, odansetron and histamine antagonists including buclizine hydrochloride, cyclizine hydrochloride and dimenhydrinate; parasympathetic depressants such as scopolamine; metopimazine; trimethobenzamide; benzquinamine hydrochloride; and diphenidol hydrochloride.

As set forth previously, the nasal delivery systems that can be used with the present invention can take various forms including aqueous solutions, non-aqueous solutions and combinations thereof. Aqueous solutions include, for example, aqueous gels, aqueous suspensions, aqueous liposomal dispersions, aqueous emulsions, aqueous microemulsions and combinations thereof. Non-aqueous solutions include, for example, non-aqueous gels, non-aqueous suspensions, non-aqueous liposomal dispersions, non-aqueous emulsions, non-aqueous microemulsions and combinations thereof.

The various forms of the delivery system set forth above can include a buffer to maintain the pH of the dopamine receptor agonist, a pharmaceutically acceptable thickening agent and a humectant. Desirably, the pH of the buffer is selected to maintain the dopamine receptor agonist in a non-ionized form. In particular, the pH of the buffer is selected to optimize the absorption of the dopamine receptor agonist across the nasal mucosa. The particular pH of the buffer, of course, can vary depending upon the particular nasal delivery formulation as well as the specific dopamine receptor agonist composition selected. Buffers that are suitable for use in the present invention include acetate, citrate, prolamine, carbonate and phosphate buffers.

With respect to the non-aqueous formulations set forth above, suitable forms of buffering agents can be selected such that when the formulation is delivered into the nasal cavity of a mammal, selected pH ranges are achieved therein upon contact with, e.g., a nasal mucosa.

In the present invention, the pH of the compositions should be maintained from about 3.0 to about 10.0. Compositions having a pH of less than about 3.0 or greater than about 10.0 can increase the risk of irritating the nasal mucosa of a recipient. Further, it is preferable that the pH of the compositions be maintained from about 3.0 to about 7.0.

The viscosity of the compositions of the present invention can be maintained at a desired level using a pharmaceutically acceptable thickening agent. Thickening agents that can be used in accordance with the present invention include methyl cellulose, xanthan gum, carboxymethyl cellulose, hydroxypropyl cellulose, carbomer, polyvinyl alcohol, alginates, acacia, chitosans and combinations thereof. The concentration of the thickening agent will depend upon the agent selected and the viscosity desired. Such agents can also be used in a powder formulation discussed above.

The compositions of the present invention can also include a humectant to reduce or prevent drying of the mucus membrane and to prevent irritation thereof Suitable humectants that can be used in the present invention include sorbitol, mineral oil, vegetable oil and glycerol; soothing agents; membrane conditioners; sweeteners; and combinations thereof. The concentration of the humectant in the present compositions will vary depending upon the agent selected.

In the present invention, other optional ingredients can also be incorporated into the nasal delivery system provided that they do not interfere with the action of the dopamine receptor agonist or significantly decrease the absorption of the dopamine receptor agonist across the nasal mucosa. Such ingredients include pharmaceutically acceptable excipients and preservatives.

To extend shelf life, preservatives can be added to the present compositions. Suitable preservatives that can be used with the present compositions include benzyl alcohol, parabens, thimerosal, chlorobutanol and benzalkonium chloride and preferably benzalkonium chloride is used. Typically, the preservative will be present in a composition in a concentration of up to about 2% by weight. The exact concentration of the preservative, however, will vary depending upon the intended use and can be easily ascertained by one skilled in the art.

The present invention provides for the compositions as described above which are administered nasally to a mammal to treat erectile dysfunction. For purposes of the present invention, "administered nasally" or "nasal administration" is intended to mean that the dopamine receptor agonists are combined with a suitable delivery system for absorption across the nasal mucosa of a mammal, preferably, a human.

A preferred embodiment of the present invention provides for a nasally administered pharmaceutical composition that includes a therapeutically effective amount of a dopamine receptor agonist dispersed in a buffer to maintain the pH of the agonist, a pharmaceutically acceptable thickening agent and a humectant. As used herein, "therapeutically effective amount" means a unit dosage of the present dopamine receptor agonist which is able to be combined with a pharmaceutically acceptable nasal delivery system and absorbed through the nasal mucosa of a mammal to produce an erection in about 1 hour, preferably in about 45 minutes, more preferably in about 30 minutes, and most preferably in 15 minutes or less which renders the intended physiological effect which is to induce a penile erection in a mammal with penile erectile dysfunction without causing substantial intolerable adverse side effects to the mammal. Preferably, the dopamine receptor agonist is selected from a group including apomorphine, chemically modified equivalents which include a pro-drug and pharmaceutical salts thereof.

Another preferred embodiment of the present invention provides for a method of treating impotence and male erectile dysfunction in a human in need of such a treatment. This method includes administering into a nasal cavity of a mammal for absorption through the nasal mucosa thereof a therapeutically effective dosage of a dopamine receptor agonist as previously set forth in combination with a nasal delivery system. The dopamine receptor agonist is preferably selected from a group including apomorphine, chemically modified equivalents which include a pro-drug and pharmaceutical salts thereof. For purposes of the present invention, the nasal delivery system can include a pharmaceutically acceptable buffer, a thickening agent and a humectant.

In another preferred embodiment of the present invention, a method is provided for administering a therapeutically effective amount of a dopamine receptor agonist to a mammal through a nasal membrane without causing substantial intolerable adverse side effects in the mammal. This method includes delivering to a nasal membrane of a mammal a dopamine receptor agonist which is dispersed in a nasal delivery system that includes a pharmaceutically acceptable buffer, a thickening agent and a humectant. In this method, the dopamine receptor agonist is effective for the treatment of a sexual dysfunction in a mammal, particularly impotence and/or erectile dysfunction in a male mammal.

Another preferred embodiment of the present invention provides for an intranasal dosage unit for treating impotency in a mammal and which does not cause substantial intolerable adverse side effects in the mammal. The intranasal dosage unit includes an effective amount of a dopamine receptor agonist in combination with a pharmaceutically acceptable intranasal carrier. This carrier includes a buffer. The pH of the buffer is selected as set forth above to facilitate dopamine receptor agonist absorption through the nasal mucosa so an erection is achieved in about 60 minutes, preferably in about 45 minutes, more preferably in about 30 minutes and most preferably in 15 minutes or less after administration.

The following examples are provided to assist in further understanding the invention. The particular materials and conditions employed are intended to be further illustrative of the invention and are not limiting upon the reasonable scope thereof.

A series of experiments were performed to illustrate features and advantages of the present invention. Several conditions were common to each experiment. For example, in Examples 1–4, apomorphine was administered to healthy male subjects who did not suffer from erectile dysfunction. Further, none of the subjects took any medication for two weeks prior to these experiments.

The following examples show that apomorphine can be nasally administered without causing substantial intolerable adverse effects. A different dosage of apomorphine was administered in each experiment to determine a preferred range of dosages having minimal adverse effects.

EXAMPLE 1

TABLE 1 shows the results of an experiment in which 1.0 mg of apomorphine HCL was nasally administered to nine male subjects.

As shown in TABLE 1, the symptoms suffered by the subjects in this experiment were generally not troublesome and of very short duration. One subject, though, suffered from moderate sneezing and another subject suffered from mild to moderate nausea. The adverse effects with nasal administration of 1.0 mg of apomorphine HCL were minimal and the severity of the adverse effects were generally not troublesome.

EXAMPLE 2

TABLE 2 shows the results of an experiment in which 0.5 mg of apomorphine HCL was nasally administered to three male subjects.

TABLE 1

NUMBER OF SUBJECTS EXPERIENCING SYMPTOMS
GIVEN BY THE DEGREE SEVERITY OF THE SYMPTOM

| SYMPTOMS EXPERIENCED | Mild, not troublesome, or of very short duration | Mild to moderate, not troublesome, of short duration | Moderate, somewhat troublesome, or persistent | Moderate, somewhat severe, troublesome, or persistent | Severe, extremely troublesome, or constantly present | TOTAL NUMBER OF SUBJECTS EXPERIENCING SYMPTOMS |
|---|---|---|---|---|---|---|
| Nasal Burning | 2 | 0 | 0 | 0 | 0 | 2 |
| Sneezing | 1 | 0 | 1 | 0 | 0 | 2 |
| Unusual Taste | 2 | 0 | 0 | 0 | 0 | 2 |
| Nausea | 1 | 1 | 0 | 0 | 0 | 2 |
| Tearing of Eyes | 1 | 0 | 0 | 0 | 0 | 1 |
| Lightheadedness | 1 | 0 | 0 | 0 | 0 | 1 |
| Tiredness | 3 | 0 | 0 | 0 | 0 | 3 |
| Congestion | 1 | 0 | 0 | 0 | 0 | 1 |
| Sweating | 1 | 0 | 0 | 0 | 0 | 1 |

TABLE 2

NUMBER OF SUBJECTS EXPERIENCING SYMPTOMS
GIVEN BY THE DEGREE OF SEVERITY OF THE SYMPTOM

| SYMPTOMS EXPERIENCED | Mild, not troublesome, or of very short duration | Mild to moderate, not troublesome, of short duration | Moderate, somewhat troublesome, or persistent | Moderate, somewhat severe, troublesome, or persistent | Severe, extremely troublesome, or constantly present | TOTAL NUMBER OF SUBJECTS EXPERIENCING SYMPTOMS |
|---|---|---|---|---|---|---|
| Nasal Burning | 2 | 0 | 0 | 0 | 0 | 2 |
| Nasal Pain | 1 | 0 | 0 | 0 | 0 | 1 |
| Unusual Taste | 1 | 0 | 0 | 0 | 0 | 1 |

It should be noted that some of the subjects of this experiment suffered from more than one symptom and one subject did not suffer from any symptoms.

One of the subjects of this experiment did not suffer any symptoms and two of the three subjects in this experiment suffered mild symptoms which were not troublesome and were of very short duration. The results of this experiment show minimal adverse effects with nasal administration of 0.5 mg of apomorphine HCL.

The results of this experiment also show that nasal administration of apomorphine HCL was effective for inducing an erection. In particular, one of the three subjects experienced an erection while another felt the beginning of an erection. cl EXAMPLE 3

TABLE 3 shows the results of an experiment in which 2.0 mg of apomorphine HCL was nasally administered to nine male subjects.

One subject of this experiment did not suffer any symptoms while the other subject experienced mild to moderate nausea and lightheadedness, which were not troublesome and were of very short duration, and moderate sneezing, which was somewhat troublesome. In particular, this subject felt like vomiting, felt lightheaded for twenty minutes after apomorphine was administered and sneezed four times. It is known in the art that the emetic effect of high dosages of apomorphine includes vomiting and therefore, it is believed that this subject suffered these symptoms due to the higher dosage of apomorphine.

TABLE 3

NUMBER OF SUBJECTS EXPERIENCING SYMPTOMS GIVEN BY THE DEGREE OF SEVERITY OF THE SYMPTOM

| SYMPTOMS EXPERIENCED | Mild, not troublesome, or of very short duration | Mild to moderate, not troublesome, of short duration | Moderate, somewhat troublesome, or persistent | Moderate, somewhat severe, troublesome, or persistent | Severe, extremely troublesome, or constantly present | TOTAL NUMBER OF SUBJECTS EXPERIENCING SYMPTOMS |
|---|---|---|---|---|---|---|
| Nasal Burning | 1 | 0 | 0 | 0 | 0 | 1 |
| Sneezing | 0 | 1 | 0 | 0 | 0 | 1 |
| Unusual Taste | 4 | 0 | 0 | 0 | 0 | 4 |
| Nausea | 3 | 0 | 0 | 0 | 0 | 3 |
| Lightheadedness | 2 | 0 | 0 | 0 | 0 | 2 |

It should be noted that some of the subjects of this experiment suffered from more than one symptom and one subject did not suffer from any symptoms.

Eight of the nine subjects in this experiment suffered from symptoms of mild degree as shown in TABLE 3. Further, the symptoms suffered by all of the subjects were not troublesome. The results of this experiment show very minimal adverse effects with nasal administration of 2.0 mg of apomorphine HCL.

The results of this experiment also show that nasal administration of apomorphine HCL was effective for inducing an erection. In particular, three of the nine subjects of this experiment had a partial erection while one subject felt an erection.

EXAMPLE 4

TABLE 4 shows the results of an experiment in which 4.0 mg of apomorphine HCL was nasally administered to two male subjects.

The results of this experiment do not show substantial adverse effects with nasal administration of 4.0 mg of apomorphine HCL.

Examples 1–4 show that apomorphine can be nasally administered at different s without substantial adverse effects and further, adverse effects are minimal dosage of apomorphine of equal to or less than 2.0 mg.

EXAMPLE 5

TABLE 5 shows the solubility and stability of apomorphine hydrochloride dispersed in several different systems.

TABLE 4

NUMBER OF SUBJECTS EXPERIENCING SYMPTOMS GIVEN BY THE DEGREE OF SEVERITY OF THE SYMPTOM

| SYMPTOMS EXPERIENCED | Mild, not troublesome, or of very short duration | Mild to moderate, not troublesome, of short duration | Moderate, somewhat troublesome, or persistent | Moderate, somewhat severe, troublesome, or persistent | Severe, extremely troublesome, or constantly present | TOTAL NUMBER OF SUBJECTS EXPERIENCING SYMPTOMS |
|---|---|---|---|---|---|---|
| Sneezing | 0 | 0 | 0 | 1 | 0 | 1 |
| Nausea | 0 | 1 | 0 | 0 | 0 | 1 |
| Lightheadedness | 0 | 1 | 0 | 0 | 0 | 1 |

TABLE 5

| System # | Composition of System | pH | Solubility (mg/mL) | Solubility Enhancement % | Improved Stability* |
|---|---|---|---|---|---|
| 1 | Water | 3.6 | 20.9 | — | — |
| 2 | Propylene Glycol | — | 84.5 | 304.3 | Yes |
| 3 | Glycerin | — | 37.4 | 78.9 | Yes |
| 4 | 50% Propylene Glycol + 50% Glycerin | — | 67.9 | 224.9 | Yes |
| 5 | Polyethylene Glycol 400 | — | 19.9 | None | Yes |
| 6 | 1.8% Ascorbic Acid + 98.2% Water | 2.3 | 25.0–30.0 | 19.6–43.5 | Yes |
| 7 | 0.2% Sodium Ascorbate + 99.8% Water | 5.0 | 20.0–25.0 | 0–19.6 | Yes |
| 8 | 0.5% Sodium Metabisulfite + 99.5% Water | 3.1 | 249 | 19.1 | Yes |

*Based on color change.

TABLE 5 shows the composition of several systems in which apomorphine as been dispersed. System #1 includes water and served as a control for comparison with System #2–System #8. TABLE 5 also shows the solubility of apomorphine HCL after it has been dispersed in the above systems. It also shows that the stability of apomorphine HCL has been improved after it has been dispersed in the systems. The improved stability of apomorphine HCL was determined based on or change of apomorphine HCL. For instance, a reduced degree of color formation after dispersion of apomorphine HCL in a system would signify improved stability.

As shown in TABLE 5, the solubility of apomorphine HCL clearly improves significantly when it is dispersed in the compositions of System #2–System #4. Further, the solubility of apomorphine HCL improved moderately when it was dispersed in the compositions of System #6–System #8.

Apomorphine HCL exhibited improved stability when dispersed in each of System #2–System #8.

The results of this experiment demonstrate that a pharmaceutical composition according to the present invention and including apomorphine dispersed in different systems as shown above, can improve the solubility and stability of apomorphine.

Thus, while there have been described what are presently believed to be the preferred embodiments of the present invention, those skilled in the art will realize that other and further embodiments can be made without departing from the spirit and scope of the invention, and it is intended to include all such further modifications and changes as come within the true scope of the claims set forth herein.

What is claimed is:

1. A pharmaceutical composition for treating sexual dysfunction in a mammalian subject comprising a therapeutically effective amount of apomorphine or a chemically modified equivalent or pharmaceutical salt thereof formulated for intranasal administration to said subject, said composition comprising one or more reducing agents selected from the group consisting of sodium metabisulfite, ascorbic acid, and sodium ascorbate and having a pH of from about 3.0 to about 3.5 yielding enhanced stability of said apomorphine or chemically modified equivalent or pharmaceutical salt thereof.

2. The pharmaceutical composition of claim 1, wherein said composition has a pH of about 3.5.

3. The pharmaceutical composition of claim 1, wherein said composition has a pH of about 3.0.

4. The pharmaceutical composition of claim 1, which is therapeutically effective following intranasal administration to said subject to prevent or reduce symptoms of erectile dysfunction in the subject.

5. The pharmaceutical composition of claim 4, which is therapeutically effective to elicit an erection in said subject within about 30 minutes following intranasal administration.

6. The pharmaceutical composition of claim 1, wherein said composition is an aqueous solution.

7. The pharmaceutical composition of claim 6, wherein said aqueous solution is selected from the group consisting of aqueous gels, aqueous suspensions, aqueous liposomal dispersions, aqueous emulsions, aqueous microemulsions and combinations thereof.

8. The pharmaceutical composition of claim 1, wherein said composition is a non-aqueous solution.

9. The pharmaceutical composition of claim 8, wherein said non-aqueous solution is selected from the group consisting of non-aqueous gels, non-aqueous suspensions, non-aqueous liposomal dispersions, non-aqueous emulsions, non-aqueous microemulsions and combinations thereof.

10. The pharmaceutical composition of claim 8, wherein said composition is a powder formulation.

11. The pharmaceutical composition of claim 10, wherein said powder formulation is selected from the group consisting of simple powder mixtures, powder microspheres, coated powder microspheres, and combinations thereof.

12. A method for treating sexual dysfunction in a mammalian subject comprising administering to said subject a therapeutically effective amount of apomorphine or a chemically modified equivalent or pharmaceutical salt thereof formulated for intranasal administration in a composition comprising one or more reducing agents selected from the group consisting of sodium metabisulfite, ascorbic acid, and sodium ascorbate, said composition having a pH of from about 3.0 to about 3.5 yielding enhanced stability of said apomorphine or chemically modified equivalent or pharmaceutical salt thereof.

13. The method for treating sexual dysfunction of claim 12, which is therapeutically effective to prevent or reduce symptoms of erectile dysfunction in the subject.

14. The method for treating sexual dysfunction of claim 13, which is therapeutically effective to elicit an erection in said subject within about 30 minutes following intranasal administration.

15. The method for treating sexual dysfunction of claim 13, wherein said composition is an aqueous solution.

* * * * *